(12) United States Patent
Wernersson et al.

(10) Patent No.: US 10,077,275 B2
(45) Date of Patent: Sep. 18, 2018

(54) PROCESS FOR PRODUCTION OF A SPIROGLYCOL

(71) Applicant: PERSTORP AB, Perstorp (SE)

(72) Inventors: Mikael Wernersson, Södertälje (SE); Linh Mong Ngo, Helsingborg (SE)

(73) Assignee: PERSTORP AB, Perstorp (SE)

( * ) Notice: Subject to any disclaimer, the term of this patent is extended or adjusted under 35 U.S.C. 154(b) by 0 days.

(21) Appl. No.: 15/738,363

(22) PCT Filed: Jun. 9, 2016

(86) PCT No.: PCT/SE2016/000033
§ 371 (c)(1),
(2) Date: Dec. 20, 2017

(87) PCT Pub. No.: WO2016/209140
PCT Pub. Date: Dec. 29, 2016

(65) Prior Publication Data
US 2018/0186809 A1 Jul. 5, 2018

(30) Foreign Application Priority Data

Jun. 23, 2015 (SE) ..................................... 1500286

(51) Int. Cl.
*C07D 493/10* (2006.01)
(52) U.S. Cl.
CPC ................................. *C07D 493/10* (2013.01)
(58) Field of Classification Search
CPC .................................................. C07D 493/10
See application file for complete search history.

(56) References Cited

U.S. PATENT DOCUMENTS

| | | | |
|---|---|---|---|
| 9,067,950 B2 | 6/2015 | Watanabe et al. | |
| 2005/0261506 A1 | 11/2005 | Watanabe et al. | |

FOREIGN PATENT DOCUMENTS

| | | | |
|---|---|---|---|
| EP | 1598357 A1 | 11/2005 | |
| JP | H0327384 A | 2/1991 | |
| JP | H-07215980 A | 8/1995 | |
| JP | 2000044569 A | 2/2000 | |
| JP | 2001-055388 A | 2/2001 | |
| JP | 2001-302674 A | 10/2001 | |
| JP | 2004224749 A | 8/2004 | |
| JP | 2005187425 A | 7/2005 | |

OTHER PUBLICATIONS

International-Type Search Report dated Dec. 18, 2015 for corresponding application No. ITS/SE15/00144.
International Search Report dated Jul. 15, 2016 in corresponding PCT Application No. PCT/SE2016/000033 and Written Opinion.
Galiano, F. R. et al., "Formation of 1, 3-Dioxanes in Water," Journal of Organic Chemistry, 1964, vol. 29, No. 11, p. 3424, ISSN 0022-3263.

*Primary Examiner* — Umamaheswari Ramachandran
(74) *Attorney, Agent, or Firm* — Polsinelli PC

(57) ABSTRACT

Disclosed is a process for production of a spiroglycol by subjecting pentaerythritol to reaction in water with hydroxypivaldehyde in presence of a catalytically active amount of at least one acid catalyst and seed particles, wherein pentaerythritol, water, at least one acid catalyst and spiroglycol seed particles are charged to a reaction vessel, equipped with heating/cooling and agitation, and under stirring heated to a predetermined reaction temperature followed by progressive addition of hydroxypivaldehyde. The spiroglycol seed particles are present in an amount of 0.5-1.0% by weight, calculated on pentaerythritol, water, acid catalyst and hydroxypivaldehyde, and the hydroxypivaldehyde is charged at a rate determined over time by monitoring growth and/or formation of yielded spiroglycol particles.

18 Claims, 2 Drawing Sheets

Graph 1 - Particle size distribution Example 1 (embodiment)

Graph 2 - Particle size distribution Example 2 (comparative)

Table 1

|  | Example 1 | Example 2 |
|---|---|---|
| 2,4,8,10-tetraoxaspiro[5.5]undecane-3,9-diethanol, % by weight | 99.35 | 99.34 |
| 2-(5,5-dimethyl-1,3-dioxane-2-yl)-2-methylpropane-1-ol, % by weight | 0.08 | 0.08 |
| 3-hydroxy-2,2-dimethylpropyl 3-hydroxy-2,2-dimethyl-propanoate, % by weight | 0.03 | 0.03 |
| 2-(9-isopropyl-2,4,8,10-tetraoxaspiro[5.5]undecane-2-yl)-2-methylpropane-1-ol, % by weight | 0.16 | 0.20 |
| 2-(9-(1-hydroxy-2-methylpropane-2-yl)-2,4,8,10-tetraoxaspiro-[5.5]undecane-3-yl)-2-methylpropyl formate, % by weight | 0.04 | 0.04 |
| (2-(1-hydroxy-2-methylpropane-2-yl)-1,3-dioxane-5,5-diyl)dimethanol, % by weight | 0.09 | 0.07 |

FIG. 3

PROCESS FOR PRODUCTION OF A SPIROGLYCOL

CROSS-REFERENCE TO RELATED APPLICATIONS

This application is a national stage application (under 35 U.S.C. § 371) of PCT/SE2016/000033, filed Jun. 9, 2016, which claims benefit of Swedish Application No. 1500286-8, filed Jun. 23, 2015, which are incorporated herein by reference in their entireties.

The present invention refers to a process for production of a spiroglycol, particularly 2,4,8,10-tetraoxaspiro[5.5]undecane-3,9-diethanol (pentaerythritol spiroglycol), by reacting pentaerythritol and hydroxypivaldehyde in presence of a catalyst and seed particles, such as pentaerythritol spiroglycol seed particles.

Spiroglycols, such as 2,4,8,10-tetraoxaspiro[5.5]undecane-3,9-diethanol (pentaerythritol spiroglycol), are dihydric alcohols, comprising a cyclic acetal structure, and are important intermediates in a number of organic synthesis, such as in production of for instance polyesters, polycarbonates, polyurethanes, antioxidants, epoxy resins, synthetic lubricants, acrylic oligomers and polymers, plasticisers, fire-retardants, and similar compounds.

Methods for production of spiroglycols are reported in for instance JP 2001055388 disclosing a synthesis of pentaerythritol spiroglycol from pentaerythritol and hydroxypivaldehyde in a water/xylene medium and in presence of sulphuric acid as catalyst. JP 2001302674 reports a multistep method for production of pentaerythritol spiroglycol from pentaerythritol, isobutyric aldehyde and formaldehyde, wherein isobutyric aldehyde and formaldehyde through aldol condensation yields hydroxypivaldehyde which subsequently is subjected to reaction with pentaerythritol.

Spiroglycols are normally and typically yielded in form of solid particles which are recovered by for instance precipitation, filtration and/or centrifugation and optionally and subsequently for instance washed and dried. Yielded spiroglycol particles are often difficult and/or expensive to recover as the amount of small particles typically is high resulting in for instance slow precipitation, filter clogging or even passing through used filters and increased liquid content in the wet filter cake. It is in JP 2796130 proposed, in order to increase the particle size, to produce spiroglycol by allowing hydroxypivaldehyde and pentaerythritol to react in water in the presence of an acid catalyst, neutralising with alkali, heat-treating the resultant slurry mixture at 120° C. or higher. The method of increasing the particle size as proposed in JP 2796130 requires a re-heating step making the process complicated and increasing the energy consumption. European patent application 1598357 disclose a method, yielding increased particle size, wherein hydroxypivaldehyde and pentaerythritol are reacted in water and in presence of an acid catalyst and spiroglycol seed particles in an amount of 1.5 to 30% by weight calculated on the reaction mixture. It is in EP 1598357, furthermore, stated that if less than 1.5% by weight of seed particles is used, the particle size of yielded spiroglycol is not increased, causing precipitation and filtration disadvantages as disclosed above, and if more than 30% by weight of seed particles is used, the amount of spiroglycol particles produced is lowered making the production efficiency poor.

BRIEF DESCRIPTION OF THE DRAWINGS

FIG. 3 is a table showing the results of GC analysis for the pentaerythritol spiroglycol prepared according to Example 1 and Example 2.

Figure 1:
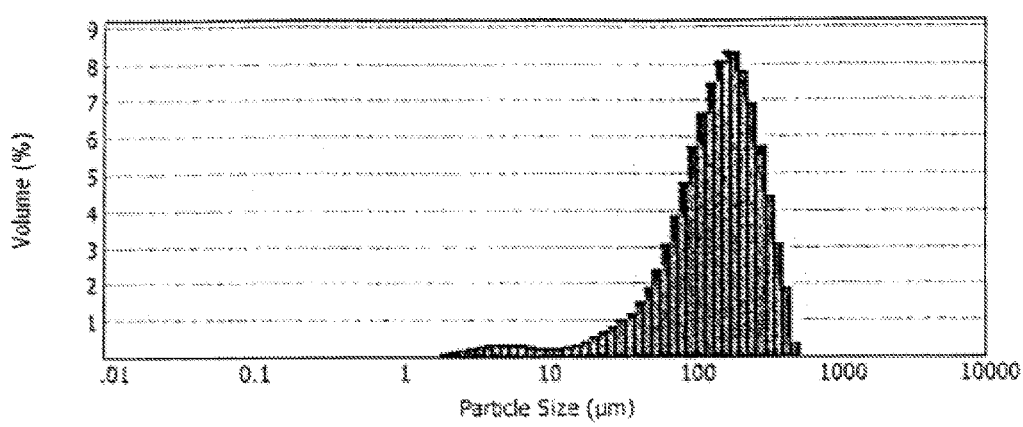
FIG. 1 is a graph showing the particle size distribution of pentaerythritol spiroglycol prepared according to Example 1.

It should be understood that the various aspects are not limited to the arrangements and instrumentality showing the figures.

It has now quit unexpectedly, especially in view of the disclosure of EP 1598357, been found that the amount of spiroglycol seed particles can be substantially reduced resulting in yet further increased particle size of yielded spiroglycol product. The process of the present invention furthermore implies reduced costs by reduced amount of seed particles. The present invention accordingly refers to a process for production of a spiroglycol by subjecting pentaerythritol to reaction in water with hydroxypivaldehyde in presence of a catalytically active amount of at least one acid catalyst and in presence of a substantially reduced amount of spiroglycol seed particles. Pentaerythritol, water, at least one acid catalyst and said spiroglycol seed particles are, in the process of the present invention, charged to a reaction vessel, equipped with heating/cooling and agitation, and under stirring heated to a predetermined reaction temperature followed by progressive addition of hydroxypivaldehyde. Said spiroglycol seed particles are preferably particles of at least one 2,4,8,10-tetraoxaspiro[5.5]undecane-3,9-dialkanol, such as 2,4,8,10-tetraoxaspiro[5.5]undecane-3,9-diethanol (pentaerythritol spiroglycol), and are present in an amount of 0.5-1.0% by weight, calculated on pentaerythritol, water, acid catalyst and hydroxypivaldehyde. Said hydroxypivaldehyde is charged at a rate determined over time by monitoring, for instance occularly and/or spectrometrically, the growth and/or formation of yielded spiroglycol particles. The reaction temperature is in preferred embodiments suitably, but not limited to, 60-100° C. and said hydroxypivaldehyde is, in likewise preferred embodiments, charged in an amount of 2-3, such as 2.1-2.5 moles/1 mole of pentaerythritol. The hydroxypivaldehyde can, for instance, be initially charged at a low rate which progressively, in one or more steps increases. A typical reaction time is 2-8 hours during which time hydroxypivaldehyde is charged followed by a 1-4 hour(s) post charging reaction time. Charged spiroglycol seed particles may, during the hydroxypivaldehyde charging, initially disappear but will reappear after approx. a couple of minutes to half an hour. The process of the present invention typically yields spiroglycol particles, especially 2,4,8,10-tetraoxaspiro[5.5]undecane-3,9-diethanol (pentaerythritol spiroglycol) having an average particle size of at least 100, such as 100-150 or even more than 150, μm.

The acid catalyst is in preferred embodiments, but not limited thereto, methane sulphonic acid, p-toluene sulphonic acid, sulphuric acid and/or hydrochloric acid and is in these embodiments suitably present at a molar ratio acid catalyst to pentaerythritol of 0.04-0.08:1.

There is no particular preference when it comes to the particle size of said spiroglycol seed particles. Seed particles having an average particle size of at least 20 μm is, however, preferred.

Yielded spiroglycol is finally preferably and suitably recovered by sedimentation, filtration and/or centrifugation and obtained reaction mixture, remain after recovery of spiroglycol, can processed or unprocessed be re-circulated to a process as herein disclosed or to any other process for production of a spiroglycol.

Without further elaboration, it is believed that one skilled in the art can, using the preceding description, utilise the present invention to its fullest extent. The following preferred specific embodiment is, therefore, to be construed as merely illustrative and not limitative of the remainder of the disclosure in any way whatsoever. In the following, Example 1 refers to an embodiment of the present invention and Example 2 to a comparative process evidencing, as given in Graphs 1 and 2 of FIG. 1 and 2, that the substantially reduced amount of seed particles, in accordance with the present invention, increases the average particle size and distribution of yielded spiroglycol without influencing the amount of formed by-products as given in Table 1 of FIG. 3.

EXAMPLE 1 (EMBODIMENT)

46.8 parts by weight of pentaerythritol (purity 99%) and 232.1 parts by weight of water were charged to a reaction vessel equipped with a heating/cooling device and agitation. The mixture was under stirring heated to 77° C. and 2.0 parts by weight of HCl (37% aq.) was, when all pentaerythritol was dissolved, added to the mixture which subsequently was heated to 90° C. 2.7 parts by weight of pentaerythritol spiroglycol seed particles (0.75% by weight calculated on pentaerythritol, water, HCl and hydroxypivaldehyde), having an average particle size of 25-35 μm, were now added and admixed for approx. 5 minutes. 81.1 parts by weight of hydroxypivaldehyde (purity 90%) were now progressively charged during 4 hours at a rate of 8-10 parts by weight/hour during the first 2 hours of reaction and 24-26 parts by weight/hour during the last 2 hours. The reaction was, when all hydroxypivaldehyde was charged, allowed to continue for a further 2.5 hours.

Obtained reaction mixture was finally cooled to ambient temperature and yielded pentaerythritol spiroglycol was recovered by filtration, washed with water and dried, thus yielding 92.3 parts by weight of purified pentaerythritol spiroglycol having an average particle size of 100-300 μm peaking at approx. 150 μm and a particle size distribution as given in attached Graph 1 of FIG. 1.

GC analysis of obtained product is in attached Table 1 of FIG. 3 given for the desired product and the main by-products.

EXAMPLE 2 (COMPARATIVE)

Example 1 was repeated with the difference that 2.0% by weight seed particles (calculated on pentaerythritol, water, HCl and hydroxypivaldehyde) was used instead of 0.75% by weight.

Figure 2:
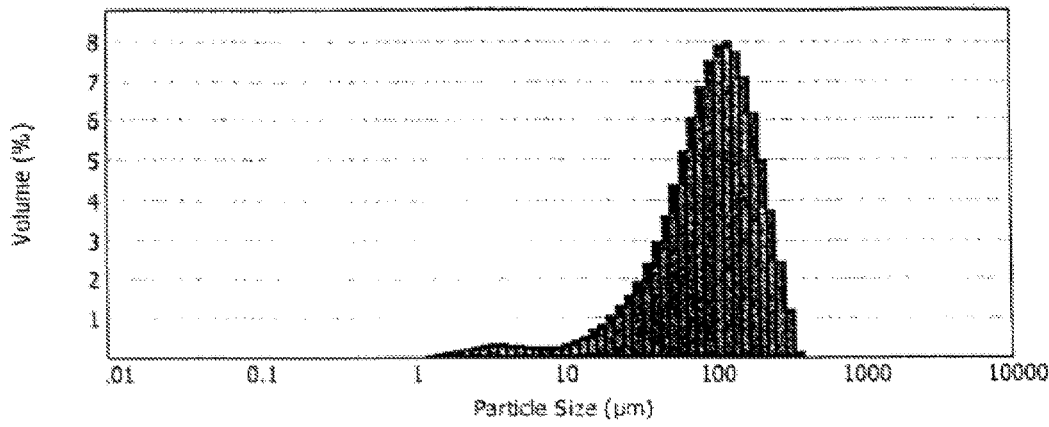
FIG. 2 is a graph showing the particle size distribution of pentaerythritol spiroglycol prepared according to Example 2.

94.3 parts by weight of purified pentaerythritol spiroglycol having an average particle size of 50-200 μm peaking at approx. 100 μm and a particle size distribution as given in attached Graph 2 of FIG. 2 was yielded.

GC analysis of obtained product is in attached Table 1 of FIG. 3 for the desired product and the main by-products.

The invention claimed is:

1. A process for production of a spiroglycol comprising subjecting pentaerythritol to reaction in water with hydroxypivaldehyde in the presence of a catalytically active amount of at least one acid catalyst and in the presence of spiroglycol seed particles, wherein pentaerythritol, water, at least one acid catalyst, and spiroglycol seed particles are charged to a reaction vessel equipped with heating/cooling and agitation, and under stirring heated to a predetermined reaction temperature followed by progressive addition of hydroxypivaldehyde, wherein said spiroglycol seed particles are present in an amount of 0.5-1.0% by weight, calculated on pentaerythritol, water, acid catalyst and hydroxypivaldehyde, and that said hydroxypivaldehyde is charged at a rate determined over time by monitoring growth and/or formation of yielded spiroglycol particles wherein the yielded spiroglycol is 2,4,8,10-tetraoxaspiro[5.5]undecane-3,9-diethanol and the spiroglycol seed particles are 2,4,8,10-tetraoxaspiro[5.5]undecane-3,9-diethanol particles.

2. The process according to claim 1, wherein said reaction temperature is between 60-100° C.

3. The process according to claim 1, wherein said hydroxypivaldehyde is charged in an amount of 2-3 moles/1 mole of pentaerythritol.

4. The process according to claim 1, wherein said acid catalyst is methane sulphonic acid, p-toluene sulphonic acid, sulphuric acid and/or hydrochloric acid.

5. The process according to claim 1, wherein said reaction is performed at a molar ratio acid catalyst to pentaerythritol of 0.04-0.08:1.

6. The process according to claim 1, wherein said yielded spiroglycol has an average particle size of at least 100 μm.

7. The process according to claim 1, wherein said yielded spiroglycol is recovered by sedimentation, filtration and/or centrifugation.

8. The process according to claim 1, wherein said spiroglycol seed particles have an average particle size of at least 20 μm.

9. The process according to claim 2, wherein said hydroxypivaldehyde is charged in an amount of 2-3 moles/1 mole of pentaerythritol.

10. The process according to claim 2, wherein said acid catalyst is methane sulphonic acid, p-toluene sulphonic acid, sulphuric acid and/or hydrochloric acid.

11. The process according to claim 2, wherein said reaction is performed at a molar ratio acid catalyst to pentaerythritol of 0.04-0.08:1.

12. The process according to claim 2, wherein said yielded spiroglycol has an average particle size of at least 100 μm.

13. The process according to claim 11, wherein said yielded spiroglycol is 2,4,8,10-tetraoxaspiro[5.5]undecane-3,9-diethanol.

14. The process according to claim 3, wherein said yielded spiroglycol is recovered by sedimentation, filtration and/or centrifugation.

15. The process according to claim 4, wherein said yielded spiroglycol is recovered by sedimentation, filtration and/or centrifugation.

16. The process according to claim 2, wherein said spiroglycol seed particles have an average particle size of at least 20 μm.

17. The process according to claim 16, wherein said yielded spiroglycol is recovered by sedimentation, filtration and/or centrifugation.

18. The process according to claim 2, wherein said spiroglycol seed particles have an average particle size of at least 20 μm.

* * * * *